United States Patent [19]
Prasad et al.

[11] Patent Number: 5,922,896
[45] Date of Patent: *Jul. 13, 1999

[54] PROCESS FOR MAKING O,S-DIMETHYL PHOSPHORAMIDOTHIOATE

[75] Inventors: Vidyanatha A. Prasad, Leawood; Klaus Jelich, Overland Park, both of Kans.; Donald K. Smith, Liberty, Mo.

[73] Assignee: Bayer Corporation, Pittsburgh, Pa.

[*] Notice: This patent is subject to a terminal disclaimer.

[21] Appl. No.: 08/988,302

[22] Filed: Dec. 10, 1997

[51] Int. Cl.$^6$ ........................................................ C07F 9/24
[52] U.S. Cl. ............................................. 558/88; 558/199
[58] Field of Search .................................................. 558/88

[56] References Cited

U.S. PATENT DOCUMENTS 3,309,266  3/1967  Magee .
3,639,547  2/1972  Magee .
4,389,350  6/1983  Lonsinger et al. .

Primary Examiner—Michael G. Ambrose
Attorney, Agent, or Firm—Joseph C. Gil; Carol Marmo

[57] ABSTRACT

The present invention provides a method for making O,S-dimethyl phosphoramidothioate. In accordance with the present process, O,O-dimethyl phosphoramidothioate is isomerized in the presence of a catalyst at a temperature of from about 35° C. to about 45° C. to form a mixture containing O,S-dimethyl phosphoramidothioate and the resultant mixture is lagered at a temperature of from about 35° C. to about 45° C. for about 3 to 6 hours. The total time for both steps is at least about 4 hours.

8 Claims, No Drawings

PROCESS FOR MAKING O,S-DIMETHYL PHOSPHORAMIDOTHIOATE

TECHNICAL FIELD OF THE INVENTION

The field of this invention is phosphoramidothioate insecticides. More particularly, the present invention pertains to a process for making O,S-dimethyl phosphoramidothioate.

BACKGROUND OF THE INVENTION

O,S-dialkyl phosphoramidothioates are effective insecticides. One particularly effective insecticide is O,S-dimethyl phosphoramidothioate (See, e.g., U.S. Pat. Nos. 3,309,266, 3,639,547 and 4,389,350, the disclosures of which are incorporated herein by reference). U.S. Pat. No. 3,309,266 discloses that O,S-dimethyl phosphoramidothioate can be made by reacting O,O-dimethyl chlorophosphorothioate with ammonia or a primary alkylamine and then heating the product of that reaction in the presence of an alkylating reagent such as an alkyl halide.

U.S. Pat. No. 3,639,547 discloses that O,S-dimethyl phosphoramidothioate can be made by reacting O,O-dimethyl phosphoramidothioate with the dimethyl ester of sulfuric acid or with a methyl ester of organic sulfonic acids. The reaction occurs at a temperature of from about 20° C. to about 100° C. In a manner similar to the method disclosed in U.S. Pat. No. 3,309,266, the O,O-dimethyl phosphoramidothioate can be made via ammoniation of a O,O-dimethyl halophosphorothioate.

With either of the above methods, the yield and purity of the formed O,S-dimethyl phosphoramidothioate are low, ranging from about 30 to 75 percent.

U.S. Pat. No. 4,389,350 describes a process for increasing the yield of the O,S-dimethyl phosphoramidothioate. The process involves i) heating the O,O-dimethyl starting material in the presence of a catalyst to a temperature of from 40° C. to 70° C., ii) arresting the heating when about 40 to 70% of the O,O-dimethyl starting material has isomerized to O,S-dialkyl product, iii) separating unreacted O,O-dialkyl starting material from the O,S-dialkyl isomerization product and iv) further treating the O,O-dialkyl starting material to effect further isomerization at a temperature of from 40° C. to 70° C. While slightly better yields are reported, the process involved is relatively complicated.

There continues to be a need in the art, therefore for a simple, efficient method for making O,S-dimethyl phosphoramidothioate.

BRIEF SUMMARY OF THE INVENTION

The present invention provides a method for increasing the yield and purity of O,S-dimethyl phosphoramidothioate. In accordance with the present process, O,O-dimethyl phosphoramidothioate is isomerized in the presence of a catalyst at a temperature of from about 35° C. to about 45° C. (and preferably about 40° C.) to form a mixture containing O,S-dimethyl phosphoramidothioate and the mixture is then lagered at a temperature of from about 35° C. to about 45° C. (and preferably about 40° C.) for about 3 to 6 hours. The total time for both steps is at least 4 hours and is preferably for from about 4 to about 10 hours (and most preferably around 6 hours). If longer times are utilized, no additional increase in yield is obtained. The use of both steps results in an at least a 4 percent increase in yield and purity over the conventional process (i.e., isomerizing at 70 to 75° C. and without lagering) and in at least a 2 percent increase in yield as well as purity over a process where the isomerization step is conducted at 70 to 75° C., followed by the lagering step.

The mixture containing O,S-dimethyl phosphoramidothioate is prepared by reacting O,O-dimethyl phosphoramidothioate in an isomerizer with a catalyst at a temperature of from about 35° C. to about 45° C. (and preferably about 40° C.). As is known in the art, in an isomerizer, the components are generally thoroughly mixed, either via the turbulence created when the components are introduced into the isomerizer or via a suitable stirring device. The time needed for this isomerization reaction can vary from about 1 to about 7 hours (and preferably for from about 1 to about 3 hours). The preferred catalyst for the isomerization reaction is dimethyl sulfate (dimethyl sulfate is a derivative of sulfuric acid).

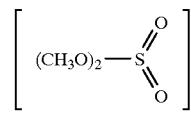

DETAILED DESCRIPTION OF THE INVENTION

In accordance with the present process, O,O-dimethyl phosphoramidothioate is isomerized in the presence of a catalyst at a temperature of from about 35° C. to about 45° C. with to form a mixture containing O,S-dimethyl phosphoramidothioate and the resultant mixture is lagered at a temperature of from about 35° C. to about 45° C. for about 3 to about 6 hours. The total time for both steps is at least about 4 hours and is preferably for from about 4 to about 10 hours. In general, the total time selected would be the time where the maximum yield is obtained. It has generally been found that times beyond 10 hours do not result in any significant increase in yield. The use of both steps results in an at least a 4 percent increase in yield and purity over the conventional process (i.e., isomerizing at 70 to 75° C. and without lagering) and in at least a 2 percent increase in yield as well as purity over a process where the isomerization step is conducted at 70 to 75° C., with a subsequent lagering step.

As is well known in the art, the term "lagering" or its grammatical equivalent, means heating with agitation. In the most preferred embodiment, the agitation in the lagering step is provided using a suitable stirring device such as an axial flow impeller, a radial-flow impeller or an axial flow impeller/baffled tank combination, operating at a speed of from 200 to 400 revolutions per minute. Typically, the two steps are conducted in separate vessels, although a single vessel could be used. The "lagering" step of the present process provides for heating a mixture containing O,S-dimethyl phosphoramidothioate at a temperature of from about 35° C. to about 45° C., with agitation for from about 3 to about 6 hours, and preferably for about 4 hours.

The reaction mixture containing O,S-dimethyl phosphoramidothioate is obtained by reacting O,O-dimethyl phosphoramidothioate in an isomerizer with a catalyst at a temperature of from about 35° C. to about 45° C. The time needed for this isomerization reaction can vary from about 1 to about 7 hours (and preferably for from about 1 to about 3 hours). The total time for both steps is at least about 4 hours and preferably for from about 4 to about 10 hours.

Suitable catalysts are the dimethyl ester of sulfuric acid or a methyl ester of an organic sulfonic acid. Exemplary such catalysts are dimethyl sulfoxide (DMSO), methyl methanealkanesulfonates such as methyl methanesulfonate, methyl ethanesulfonate, methyl propanesulfonate, methyl hexanesulfonate, methyl benzenesulfonate, methyl toluenesulfonate, methyl xylenesulfonate, methyl napthylsulfonate, methyl p-chlorophenylsulfonate, methyl o-chlorophenylsulfonate, methyl m-bromophenylsulfonate, methyl p-bromophenylsulfonate and methyl chloronapthylsulfonate. Dimethyl sulfate is most preferred.

O,O-Dimethyl phosphoramidothioate is used to make O,S-dimethyl phosphoramidothioate and can be prepared using any process well known in the art. In one embodiment, O,O-dimethyl phosphoramidothioate is made via ammoniation of a O,O-dimethylhalophosphorothioate such as O,O-dimethylchlorophosphorothioate (DMPCT). Typically, the DMPCT in an aromatic solvent such as toluene, benzene or xylene is reacted with ammonia. The solvent is removed prior to the methylation-isomerization step set forth above.

The Example that follows illustrates a preferred embodiment of the present invention and is not limiting of the specification and claims in any way.

EXAMPLE 700 parts by weight of O,O-dimethyl phosphoramidothioate was introduced into a reactor equipped with a stirrer. The reactor was heated to 40° C. with stirring of the starting material. Once the O,O-dimethyl phosphoramidothioate had reached 40° C., 30.1 parts by weight of dimethyl sulfate were added. The temperature was maintained at 40° C. and samples of product were taken after 2 hours, 4 hours, 6 hours and 24 hours. The content of O,S-dimethyl phosphoroamidothioate was determined for each sample in each part.

The net yields of O,S-dimethyl phosphoramidothioate produced were as follows:

2 hours: 82%
4 hours: 82.4%
6 hours: 83.4%
24 hours: 83.2%

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for making O,S-dimethyl phosphoramidothioate comprising:
    a) isomerizing O,O-dimethyl phosphoramidothioate in the presence of a catalyst at a temperature of from about 35° C. to about 45° C. to form a mixture containing O,S-dimethyl phosphoroamidothioate, and
    b) lagering said isomeric mixture of O,S-dimethyl phosphoramidothioate at a temperature of from about 35° C. to about 45° C. for from about 3 to about 6 hours, wherein agitation of said lagering step is provided by a stirring device at a speed of from about 200 to about 400 revolutions per minute,
with the total time of steps a) and b) being at least about 4 hours.

2. The process of claim 1, wherein the total time of steps a) and b) is from about 4 to about 10 hours.

3. The process of claim 1, wherein the total time of steps a) and b) is about 6 hours, and wherein both of said temperatures are about 40° C.

4. The process of claim 1 wherein the catalyst is dimethyl sulfate.

5. The process of claim 4 wherein the O,O-dimethyl phosphoramidothioate is made by ammoniating O,O-dimethylchlorophosphorothioate.

6. A process of making O,S-dimethyl phosphoramidothioate comprising the steps of:
    a) ammoniating O,O-dimethylchlorophosphorothioate to form O,O-dimethyl phosphoramidothioate;
    b) isomerizing O,O-dimethyl phosphoramidothioate in the presence of a catalyst at a temperature of from about 35° C. to about 45° C. to form a mixture containing O,S-dimethyl phosphoramidothioate, and
    c) lagering said mixture containing O,S-dimethyl phosphoramidothioate at a temperature of from about 35° C. to about 45° C. for from about 3 to about 6 hours,
with the total time of steps b) and c) being at least about 4 hours.

7. The process of claim 6, wherein the total time of steps b) and c) is from about 4 to about 10 hours.

8. The process of claim 6, wherein the total time of steps b) and c) is about 6 hours, and wherein both of said temperatures are about 40° C.

* * * * *